United States Patent [19]

Montag et al.

[11] Patent Number: 5,472,411
[45] Date of Patent: Dec. 5, 1995

[54] ANKLE JOINT ORTHOSIS WITH U-SHAPED JOINT COLLAR AND FLEXIBLE WEB

[75] Inventors: Hans-Jürgen Montag, Amerang; Andreas Albrod, Hamburg; Hugh Andrews, Kölln-Reisiek; Stefan Bodenschatz, Buxtehude; Anette Rundkowski, Hamburg, all of Germany

[73] Assignee: Beiersdorf AG, Hamburg, Germany

[21] Appl. No.: 251,323

[22] Filed: May 31, 1994

[30] Foreign Application Priority Data

Jun. 4, 1993 [DE] Germany .............. 43 18 588.6

[51] Int. Cl.⁶ ..................................................... A61F 5/00
[52] U.S. Cl. .............................. 602/23; 602/27; 128/882
[58] Field of Search .................................. 128/869, 882; 602/23, 24, 27, 60, 61, 62, 63

[56] References Cited

U.S. PATENT DOCUMENTS

| | | | |
|---|---|---|---|
| 4,313,433 | 2/1982 | Cramer | 602/27 |
| 4,323,058 | 4/1982 | Detty | 602/27 |
| 4,597,395 | 7/1986 | Barlow | 602/27 |
| 4,938,222 | 7/1990 | Bier | 602/27 |
| 4,962,768 | 10/1990 | Stromgren | 602/27 |
| 5,000,195 | 3/1991 | Neal | 602/27 |
| 5,016,623 | 5/1991 | Krahenbuhl | 602/27 |
| 5,099,860 | 3/1992 | Amrein | 128/882 |
| 5,139,479 | 8/1992 | Peters | 602/27 |

FOREIGN PATENT DOCUMENTS

| | | |
|---|---|---|
| 3909922 | 2/1990 | Germany . |
| 3840714 | 6/1990 | Germany . |
| 4112069 | 10/1992 | Germany . |

*Primary Examiner*—Michael A. Brown
*Attorney, Agent, or Firm*—Friedrich Kueffner

[57] ABSTRACT

The ankle joint orthosis includes a U-shaped joint collar having a web of a flexible material proceeding underneath the foot. The joint collar (20) includes two ankle splints (21,121), which are connected by means of a web (22) proceeding below the heel of the foot and, on the rear, while leaving the heel and the attachment of the Achilles tendon uncovered, by a wide band (23) as well as at the front, within its upper ergion, by means of a longitudinally variable belt strap (25,25') and a metatarsal portion (30), which is medially and laterally provided with flaps, which laterally and medially embrace the borders of the foot and constitute the connection for two belt straps (40,140) and a transverse cross strap (50) connecting the flaps. On the side of the sole of the foot, the metatarsal portion (30) is connected with the web (22) of the joint collar (20) by means of a highly flexible web (35) acting as an articulation. The cross belt straps (40;140) are mounted in such a way that one cross belt strap (140) is carried from the medial flap via the proximal dorsum pedis to the outer ankle splint (21) and is fastened to the same and the other cross belt strap (40) is carried from the lateral flap (31) to the inner ankle splint (121) and is fastened to the same (FIG. 1).

10 Claims, 3 Drawing Sheets

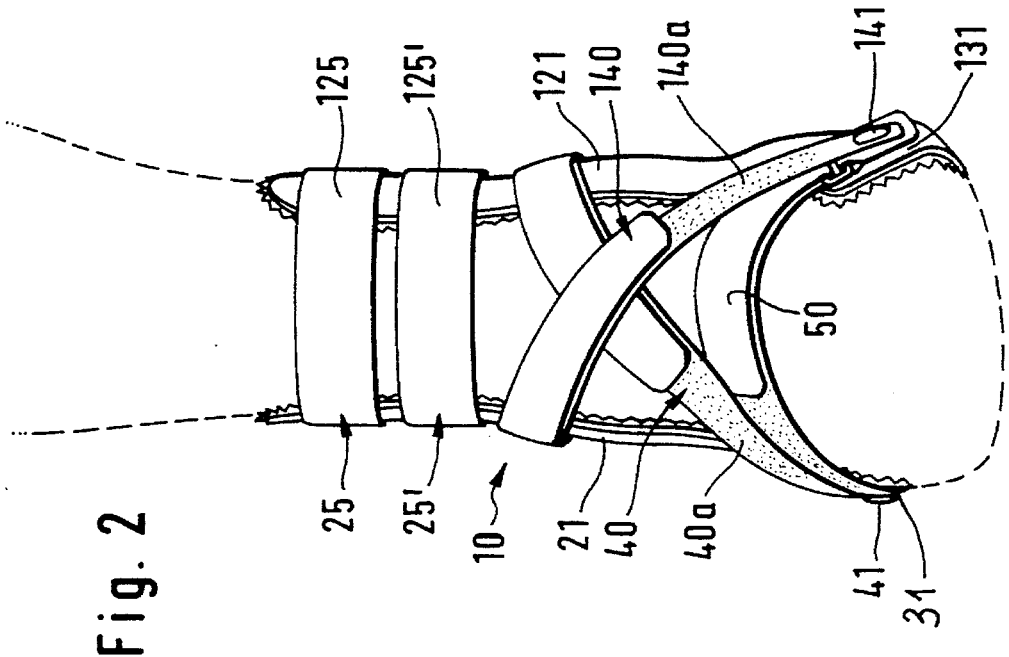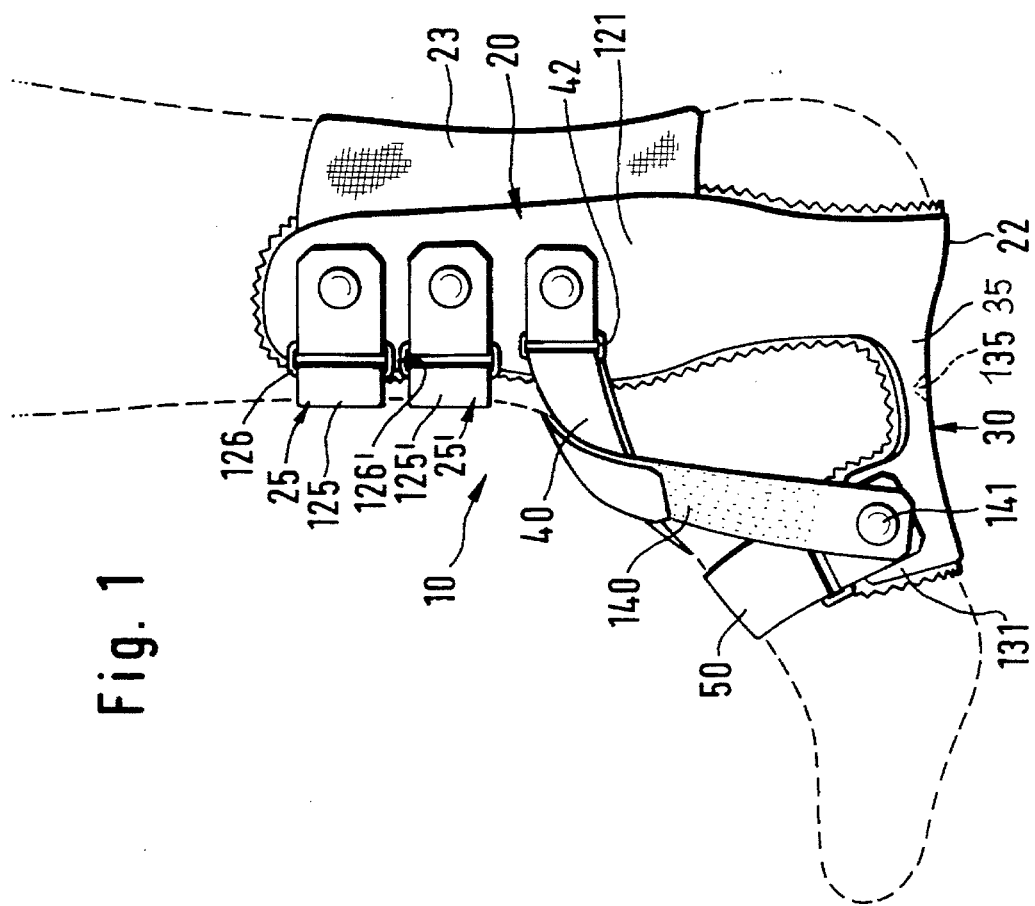

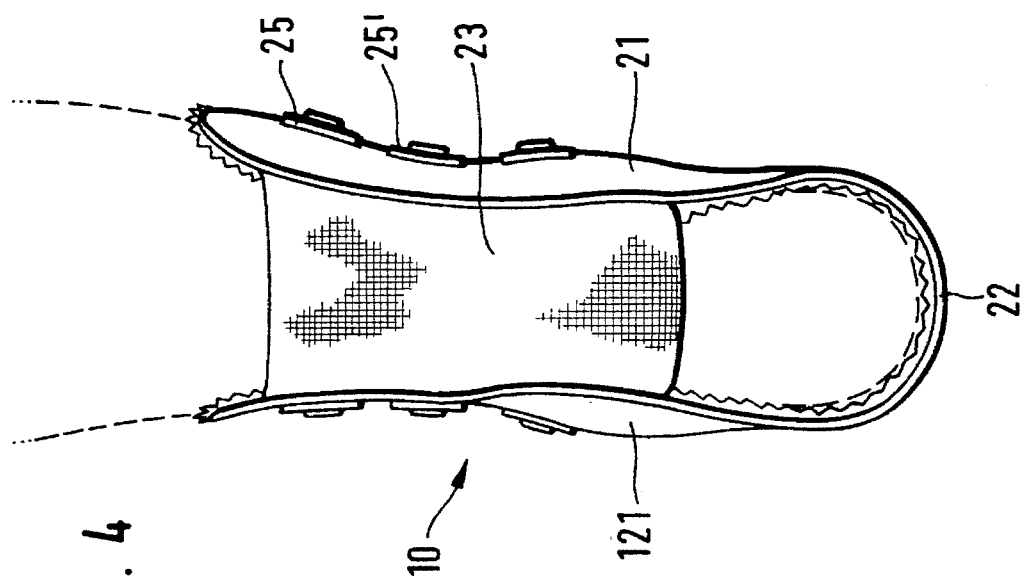
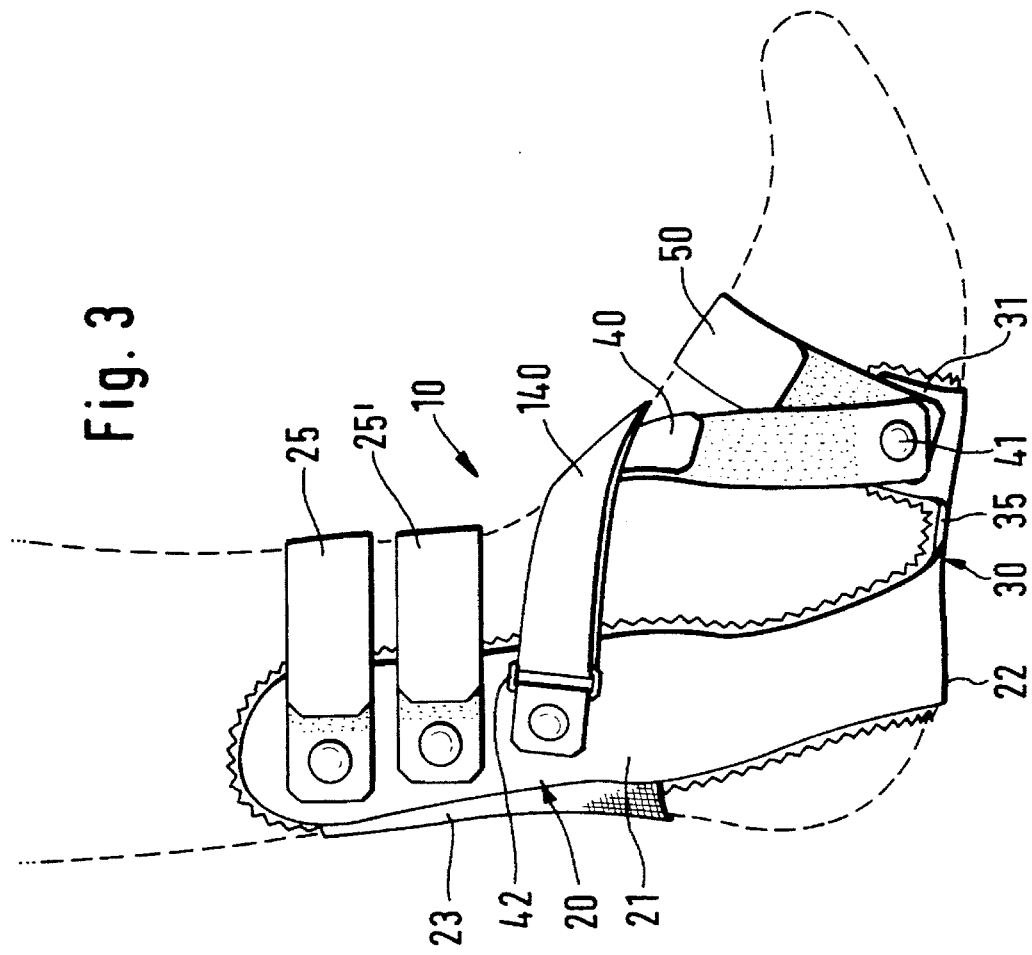

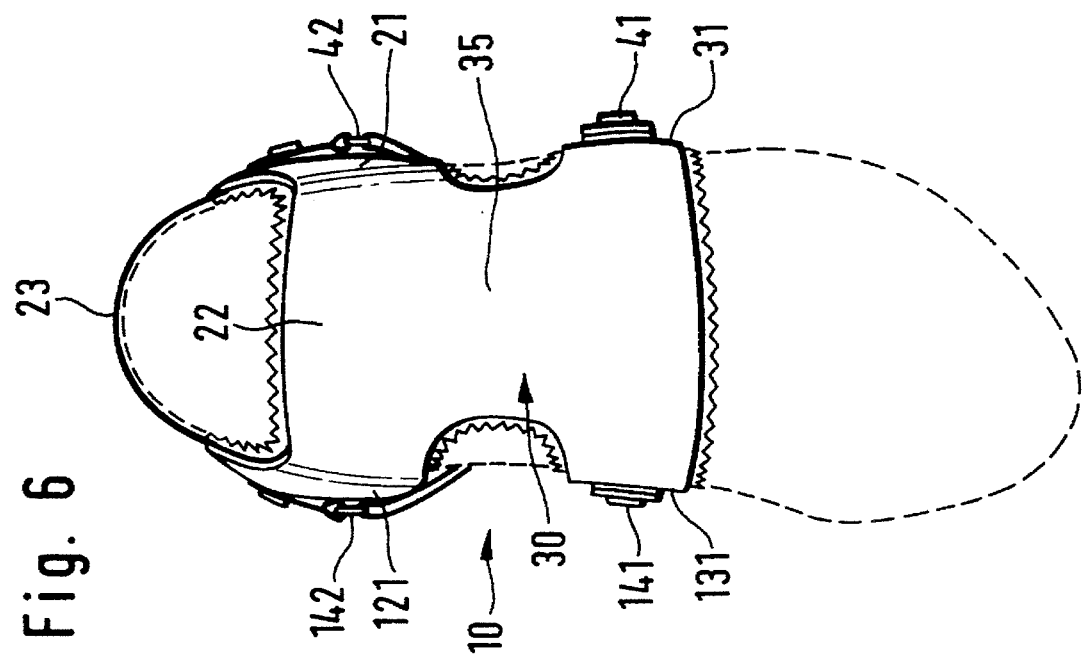
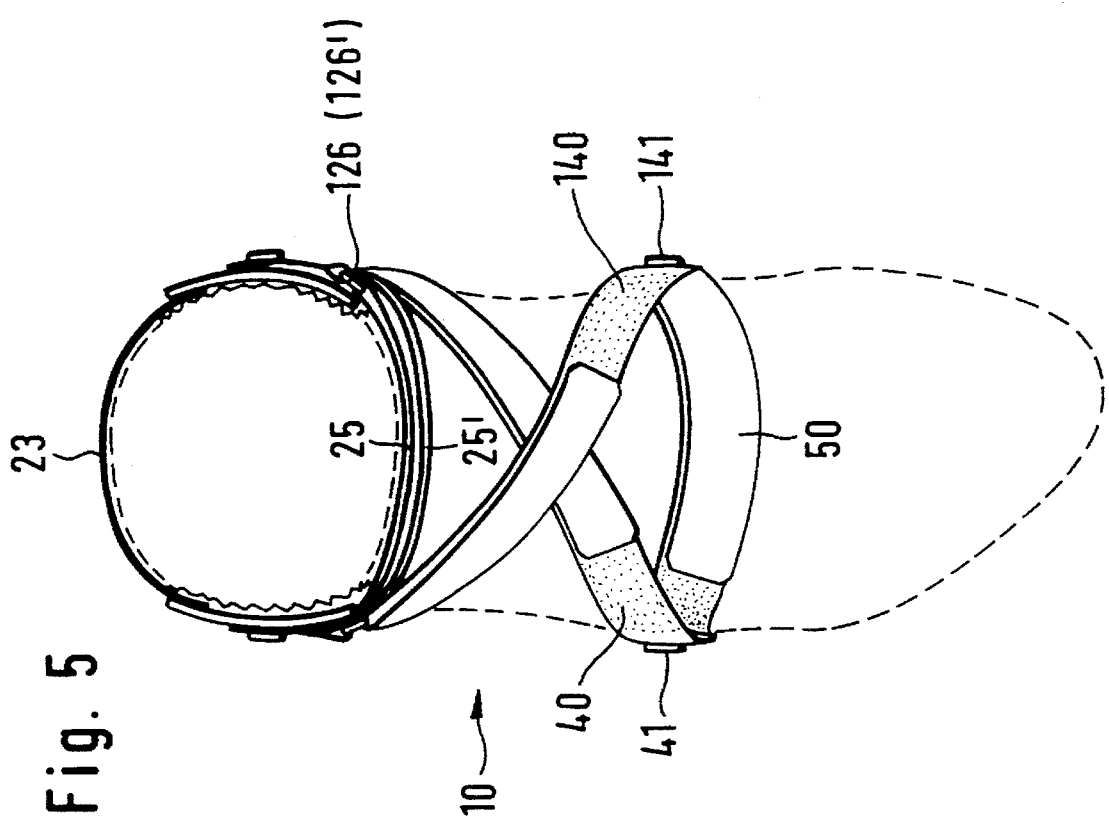

ANKLE JOINT ORTHOSIS WITH U-SHAPED JOINT COLLAR AND FLEXIBLE WEB

The present invention relates to an ankle joint orthosis, more particularly for the early functional treatment of fresh fibular ligament ruptures and of severe tarsal distorsions, in which case this orthosis comprises a U-shaped joint collar or sleeve having a web of a flexible material proceeding underneath the foot.

BACKGROUND OF THE INVENTION

From the DE-A-38 40 714, an ankle joint orthosis having a U-shaped supporting arm is known, whose legs converge underneath the footh into a web, reach past the ankles and, in their terminal region, are held together by means of a fastening strap. In this case the outer leg is carried upwardly laterally before its ankle and the inner leg, in comparison with the other leg, is carried upwardly before the Achilles tendon. Both legs are carried in the direction of the web up to a position before the heel and proceed upwardly in the direction of their ends in such a way that they rise upwardly next to the tibial edges approximately parallel to the same, while a fastening strap is fitted in the lower region of the legs which proceeds from the one leg via the instep obliquely upward to the other leg so as to be fixable upon the same, engages around the Achilles tendon above the ankles and terminates on the instep while crossing itself on the other leg in a retaining portion. With a thusly constructed ankle joint orthosis it is intended to prevent the twisting or distorting above all into the laterally-anterior direction, thus into apes equinus position. Since the U-shaped supporting arm of this ankle joint orthosis is, with its outer leg, carreid upward lateralyl in front of the ankle and, with its inner leg, in front of the Achilles heel and is held together by a web proceeding underneath the foot, the medial border of the metatarsus is not included so that the employment of this orthosis is restricted.

The DE-A-39 09 922 describes a foot fixation splint. This foot fixation splint serves particularly for the post-operative treatment of an injured ankle joint with a foot portion that engages around the foot, which is followed by a retaining portion provide d with closing bands, said retaining portion reaching upwardly as far as into the region of the calf. In this case the retaining portion is divided into two side portions which link up with the foot portion and are constructed in a shell-like fashion. Each of the regions of the side portion covering the ankle of the foot is provided with a window-like cutout. The region of the Achilles tendon on the foot portion and on the retaining portion is left uncovered in this case. The adjustable and fixatable tape-like closing bands are comprised of a non-extensible material, while one closing band on the foot portion is disposed in such a way that it, while engaging over the dorsum pedis, fixates the first metatarsal ray against supinatory ascendance. With such a foot fixation splint it is intended, on the one hand, to achieve a perfect immobilization of the foot to be treated and, on the other hand, to avoid the drawbacks of a plaster cast for, subsequent to injuries and operations on the external joint ligaments, the foot is frequently put in plaster for immobilization, in which case a post-operative treatment of surgical wounds is not possible owing to numerous serious disadvantages. In this foot fixation splint one sets out from a U-shaped joint collar or sleeve having a full-surface sole portion which covers the midfoot and forefoot up to the ball of the small toe, in which case, however, no adequate flexibility exists within the metatarsal region.

According to the U.S. Pat. No. 5,000,195, a device for splinting the ankle is known which brings about a rigid angular alignment of the ankle in relation to the leg as well as a compression so as to reduce swellings following a pulled tendon or a rupture of the tendon. This device is comprised of an elongated, substantially non-yielding flat member plate inclusive of a first and a second terminal flap which are interconnected by means of a center zone, said center zone being configured in such a way that, when the splint is applied, it lies underneath the arch of the foot, whereas the terminal flaps are disposed so as to proceed upwardly on both oppositely located sides of the ankle and, from the arch of the foot upward, at least beyond the lateral and central malleolus, so as to cover the ankle, in which case the rear borders of the terminal flaps are in a separate, but side-by-side position along the rear of the ankle and the front borders of the terminal flaps are in a separate, but side-by-side position along the front of the ankle. The center zone possesses a lesser width than the terminal flaps and is constituted of an arcuate depression along the central front border of the member plate and of a cutout along the central rear borders of the member plate, in which case the arcuate depression on the front border extends downwardly and rearwardly from the upper part of the surface of the dorsum pedis along the opposite sides of the ankle and thus lies below the arch of the foot in such a way that a dorsal flexural force is exerted against the ankle when the front borders of the terminal flaps are drawn toward each other. In addition, elastic means are provided which connect the first and the second terminal flap along their respective rear borders from their topmost ends up to a point located approximately next to their stitched cutouts, as well as rigid means, which interconnect the first and the second terminal flap detachably and adaptably along their respective side-by-side arranged lateral borders from the top ends of the same up to approximately the center of the dorsum pedis. Behind this the device comprises a U-shaped joint collar possessing a flexible web proceeding underneath the foot, outer and inner ankle splints which are interconnected via a heel web, depressions for accommodating the ankle, a rearward heel recess as well as a wide connecting strap between the splints and, furthermore, a longitudinally variable belt strap at the front within the top area, however, in this known device no provision is made for a construction of the sole portion of the device which comprises a splint connection web and a further highly flexible, articulatedly effective web which passes into the metatarsal portion with lateral flaps for the securing of belt, especially since, with the aid of this device, it is substantially intended to merely achieve a compression for the subsidence of swellings.

The present invention is based upon the technical problem of providing an ankle joint orthosis for an early functional treatment of fresh fibular ligament ruptures and of severe tarsal distorsions, with the aid of which a lateral and medial stabilization of the upper and lower ankle joint is achieved, whereby both inversion traumata as well as eversion traumata are prevented.

This technical problem is resolved by means of the features characterized in the claim 1.

SUMMARY OF THE INVENTION

According to the construction in accordance with the invention, the ankle joint orthosis is comprised of a U-shaped joint collar or sleeve fabricated from a thermoplastic material which is composed of an outer ankle splint and an inner ankle splint. These ankle splints are interconnected by means of a web proceeding underneath the heel which is fabricated from the same material. In addition, the ankle splints possess anatomically correct recesses for adaptation to the ankle contours and for an anatomically correct fit. A further element of the orthosis is its metatarsal portion which is likewise fabricated from thermoplastic material. This part of the orthosis runs obliquely underneath the sole of the foot proximally to the capitula of the metatarsal bones I–V and is constructed both medially as well as laterally in a flap-like manner. The thusly constructed flaps embrace the borders of the foot both outwardly and inwardly. On the one hand they guide the metatarsus, on the other hand they serve for the attachment of cross belt straps and transverse belt straps. In this case the metatarsal portion is connected on the side of the sole of the foot by means of a highly flexible web likewise fabricated from thermoplastic material. This web possesses the function of an articulation and operates analogously to a film hinge. The axis of rotation of this joint constructed in the highly flexible web proceeds from dorsomedial to antero-lateral and forms an angle of approximately 10° to the longitudinal axis of the foot and this in accordance with the anatomy of the lower ankle joint. Expediently the ariculated web possesses an increased rigidity on the medial side.

By preference, the parts of the ankle joint orthosis fabricated from thermoplastic material are coated on the skin side in such a way that an intimate contact with the skin is brought about and remains maintaiend while the ankle joint orthosis is worn, and this along the lines of proprioception, that is to say to the effect that a constant perception and control of the actual load on and position of the joint on the part of the wearer of the orthosis is ensured.

The ankle splints are interconnected on the rear by means of a wide band while the heel and the attachment of the Achilles tendon are left uncovered. This band is distinguished in that it possesses a defined, limited extensibility and consequently prevents a forward dislocation of the ankle splints under load.

On the front, the ankle splints, within their upper region, are interconnected by means of two transversally proceeding belt straps which are expediently constructed in the form of Velcro tapes. In this case, each Velcro tape is hinged onto the lateral ankle splint, drawn through an eye here, drawn lateralyl and is then close by means of Velcro fastening. from this results a continuous, individual adaptation of the ankle joint orthosis to the malleolar mortice and its circumference.

The medial and the lateral flap of the metatarsal portion are interconnected with the aid of a belt strap proceeding transversally across the dorsum pedis likewise constructed in the form of a Velcro tape, whereby a secure fixation of the metatarsus in the ankle joint orthosis is achieved. This Velcro tap is hinged onto the lateral flap, is passed through an eye on the medial flap and is then closed by means of Velcro fastening. An individual adaptation of the orthosis is possible thereby.

One cross belt strap each is rotatably hinged onto the medial and the lateral flap of the metatarsal portion. These cross belt straps, too, are preferably constructed in the form of Velcro tapes. In this case, a Velcro tape proceeds from the medial flap via the proximal dorsum pedis to the outer ankle splint, upon whose outside a rotatably supported eye is to be found. The Velcro tape is drawn through this eye and secured by means of Velcro fastening. The other Velcro tape is carried in the same manner from the lateral flap to the inner ankle splint. By virtue of this cross bridle-like running of the Velcro tape with a continuous, individual adjustment possibility, an effective guidance and strapping of the metatarsus results.

The following advantages are achieved with the ankle joint orthosis:

Complete embracing and guidance of the entire metatarsus from medial and lateral.

An anatomically correct articulation web—which takes the axes of the upper and the lower ankle joint into account—between the joint collar and the metatarsal portion additionally counteracts a supination trauma by means of its medial stiffening.

The elastic band connecting the two ankle splints on the rear possesses a defined, limited elasticity.

The way in which the cross belt straps on the side of the dorsum pedis are carried in connection with the articulation web brings about a secure guidance and strapping of the metatarsus.

The skinn-side coating of the plastic components causes a slip-proof fit of the ankle joint orthosis on the foot.

With the aid of the constructional elements, such as the U-shaped joint collar and the metatarsal portion hinged thereonto, the ankle joint orthosis brings about a lateral and medial stabilization of the upper and lower ankle joint, that is to say, both inversion traumata (supination, plantar flexion, adduction) as well as eversion traumate (pronation, dorsal flexion, abduction) are prevented. The web on the metatarsal portion possessing the medial reinforcement additionally prevents a supination trauma. in the process, the joints are retained in a physiological position. The ankle joint orthosis permits a high degree of mobilization as is necessary for the functional treatment of the ankle joint; but it also guarantees, by the defined, limited elasticity, a secure stabilization of the injured ankle joint. That is why the ankle joint orthosis is particularly well suited for the early functional treatment of fresh fibular ligament ruptures both in primary conservative therapy as well as after the surgical care of the ligament injury. Moreover, the ankle joint orthosis is suited for the therapy of severe tarsal distorsions.

Advantageous constructiond of the invention are characterized in the subclaims.

BRIEF DESCRIPTION OF THE DRAWINGS

In the following the invention will be explained in greater detail with the aid of diagrammatical drawings of an embodiment example. The drawings depict an ankle joint orthosis in FIG. 1 in a medial view, FIG. 2 in a front view, FIG. 3 in a lateral view, FIG. 4 in a dorsal view, FIG. 5 in a view from the top, and FIG. 6 in a plantar view.

DETAILED DESCRIPTION OF THE PREFERRED EMBODIMENT

According to the FIGS. 1 through 6, the ankle joint orthosis 10 is comprised of a joint collar 20 with an outer ankle splint 21 and an inner ankle splint 121. The two ankle splints 21,121 are interconnected by means of a web 22 proceeding underneath the heel of the foot. At the rear, the two ankle splints 21,121, while leaving the heel and the attachment of the Achilles tendon uncovered, are interconnected by means of an elastic band 23 preferably possessing a width of 12 cm and possessing a defined, limited extensibility so that, in the applied state of the ankle joint orthosis 10, the two ankle splints 21,121 fit firmly against the two ankle sides. This band 23, with regard to its length, possesses a transverse elasticity.

Both ankle splints 21,121 possess anatomically correct depressions and this for adaptation to the ankle contours and for an anatomically correct fit (FIGS. 1 and 3).

Within the front area, the two ankle splints 21,121 of the joint collar 20 are interconnected by means of at least one longitudinally variable belt strap 25 or 25', this will be dealt with still in greater detail hereinafter.

A metatarsal portion 30 is formed onto the web 22 of the joint collar 20 which is constructed in a flap-like fashion medially and laterally. This metatarsal portion 30 is connected to the web 22 of the joint collar by means of a web 35 which is constructed in the form of an articulation web.

The two flaps 31,131 of the metatarsal portion 30 embrace the foot borders laterally and medially (FIGS. 1 and 3). In addition, both flaps 31,131 are constructed for the connection of two cross belt straps 40,140 and of a transverse belt strap 50. The two flaps 31.131 are interconnected via the transverse belt strap 50.

On the side of the sole of the foot, the metatarsal portion 30 is connected by means of a highly flexible web 35 acting as an articulation to the web 22 of the joint collar 20. This articulation web 35 possesses an increased rigidity on the medial side (FIG. 6).

One cross belt strap 40,140 each is hinged onto the medial and lateral flap 31,131 of the metatarsal portion 30 at 41, 141. In this case the cross belt strap 140 is carried from the medial flap 131 across the proximal dorsum pedis to the outer ankle splint 21 and is fastened to the same, while the other cross belt strap 40 is carried from the lateral flap 31 to the inner ankle splint 121 and is likewise fastened to the same (FIG. 2). The transverse belt strap 50 is expediently hinged with its ends likewise at 41,141 onto the flaps 31,131 of the metatarsal portion 30.

By preference the highly flexible web 35 of the metatarsal portion 30 possesses a width of approximately 5 cm. In this case the axis of rotation of this articulation formed by the web 35 proceeds from dorso-medial to antero-lateral and forms, with the longitudinal axis of the foot, an angle of approximately 10° according to the anatomy of the lower ankle, in which case also other angular positions are possible.

The effect of the web 35 of the metatarsal portion 30 of acting as an articulation is based up on the circumstance that the web 35 is fabricated from a thermoplastic material, in which connection it is possible to additionally increase the articulation effect by means of a notch 135 proceeding transversally to the longitudinal direction of the foot so that the function of a film hinge is achieved. In this way a high degree of mobility of the foot is achieved (FIG. 1).

Also the joint collar 20 and the metatarsal portion 30 are comprised of a thermoplastic material. The components of the ankle joint orthosis 10 which are comprised of the thermoplastic material are, on the side of the skin, provided with a skin contact-maintaining coating. This coating possesses a great skin kindness and may, by way of example, be comprised of a pile fabric or a fabric having a brushed-up surface.

In the embodiment example depicted in the FIGS. 1 through 6, the two ankle splints 21,121 of the joint collar 20 are interconnected at the front by means of two superposedly arranged belt straps 25,25'. These belt straps 25,25', which are of identical construction, comprise transversally proceeding Velcro tapes 125, 125'. These Velcro tapes 125, 125' are at one end hinged onto the outer ankle splint 21 and, from there, carried to the inner ankle splint 121 which is provided with eyes 126, 126', through which the Velcro tapes are drawn. Each Velcro tape 125, 125' is then secured with its free end by means of the Velcro fastening to the tape end located therebelow.

The cross belt straps 40,140 secured to the flaps 31,131 of the metatarsal portion 30 and carried to the ankle splints 21,121 of the joint collar which are also secured there, are variable in their lengths and are preferably constructed in the form of Velcro tapes 40a, 140a(FIG. 2). One Velcro tape 40a or 140a each is rotatably hinged onto the lateral and the medial flap 31,131 of the metatarsal portion 30 at 41,141. The Velcro tape 140a is carried from the medial flap 131 to the outer ankle splint 21 and, on the outside of the same, passed through an eye 42 rotatably secured to the outer ankle splint 21. The end of the Velcro tape 140a passed through the eye 42 is then secured by means of Velcro fastening to the Velcro tape section located in each case therebelow. The other Velcro tape 40a is carried from the lateral flap 31 of the metatarsal portion 30 to the inner ankle splint 121, on whose outside a rotatable eye 42 is secured, through which the Velcro tape 40a is drawn and secured by means of Velcro fastening in a manner corresponding to the securing of Velcro tape 140a.

What is claimed is:

1. An ankle joint orthosis, more particularly for the early functional treatment of fresh fibular ligament ruptures and of severe tarsal distortions, the ankle joint orthosis comprising a U-shaped joint collar having a front side and a rear side, the joint collar comprising an outer ankle splint and an inner ankle splint, a web of a flexible material extending underneath the heel of the foot connecting the outer ankle splint and the inner ankle splint, the ankle splints being additionally interconnected on the rear side by means of a wide band which leaves the heel and the Achilles tendon attachment uncovered, and on the front side and in an upper region by means of at least one longitudinally variable belt strap, the ankle splints having anatomically adapted and configured recesses, further comprising a metatarsal portion extending transversely underneath the planta proximally to the capitula of the metatarsal bones, the metatarsal portion comprising medial and lateral flaps which embrace the border of the foot both laterally and medially, the medial flap and the lateral flap being interconnected by means of a transverse cross strap, further comprising a highly flexible bridge portion for connecting on the side of the planta the metatarsal portion to the web of the joint collar, the bridge portion acting as an articulation, a cross belt strap each being hinged to the medial and lateral flaps of the metatarsal portion, wherein a first of the cross belt straps extends from the medial flap via the proximal dorsum pedis to the outer ankle splint and is secured to the outer ankle splint and a second of the cross belt straps extends from the lateral flap to the inner ankle splint and is attached to the inner ankle splint.

2. The ankle joint orthosis according to claim 1, wherein the highly flexible bridge member has a width of approximately 5 cm.

3. The ankle joint orthosis according to claim 1, wherein the articulation formed by the highly flexible bridge member has an axis of rotation, the axis of rotation extending from dorso-medial to antero-lateral and includes with the longitudinal axis of the foot an angle of approximately 10° so as to conform to the anatomy of the lower ankle joint of the foot.

4. The ankle joint orthosis according to claim 1, wherein the joint collar and the metatarsal portion are of thermoplastic material.

5. The ankle joint orthosis according to claim 4, wherein the joint collar and the metatarsal portion of thermoplastic material have on the side of the skin of the foot a coating for maintaining contact with the skin.

6. The ankle joint orthosis according to claim 1, wherein the wide band interconnecting the two ankle splints on the rear side have a transverse elasticity.

7. The ankle joint orthosis according to claim 6, wherein the wide band has a width of approximately 12 cm.

8. The ankle joint orthosis according to claim 1, wherein the ankle splints are at the front side interconnected by means of two belt straps in the form of transversely extending hook and loop tapes, and wherein one end of each belt strap is hinged to the outer ankle splint, wherein the belt straps extend from the outer ankle splint to the inner ankle splint and extend through eyes attached to the inner ankle splint, are pulled laterally upwardly and are secured by means of hook and loop fastening.

9. The ankle joint orthosis according to claim 1, wherein the cross belt straps connected to the flaps of the metatarsal portion are constructed in the form of hook and loop tapes, wherein each ankle splint has a rotatable eye on an outside thereof, wherein one of the cross belt straps extends from the medial flap toward and through the rotatable eye of the outer ankle splint and is closed by means of hook and loop fastening, while the other cross belt strap extends from the lateral flap to and through the rotatable eye of the inner ankle splint and is closed by means of hook and loop fastening.

10. The ankle joint orthosis according to claim 1, wherein the bridge member has an increased rigidity on the medial side.

* * * * *